United States Patent [19]

Meyer

[11] Patent Number: 4,998,527

[45] Date of Patent: Mar. 12, 1991

[54] ENDOSCOPIC ABDOMINAL, UROLOGICAL, AND GYNECOLOGICAL TISSUE REMOVING DEVICE

[75] Inventor: William F. Meyer, Walnut, Calif.

[73] Assignee: Percutaneous Technologies Inc., Walnut, Calif.

[21] Appl. No.: 498,946

[22] Filed: Mar. 26, 1990

Related U.S. Application Data

[63] Continuation-in-part of Ser. No. 387,577, Jul. 27, 1989, abandoned.

[51] Int. Cl.[5] .............................................. A61B 1/00
[52] U.S. Cl. .......................................... 128/6; 128/4; 604/22; 604/24; 606/46
[58] Field of Search ................... 128/4, 6; 604/22, 24; 606/46, 47

[56] References Cited

U.S. PATENT DOCUMENTS

| | | | |
|---|---|---|---|
| 2,888,928 | 6/1915 | Seiger | 606/49 X |
| 3,024,787 | 3/1962 | Birch et al. | 604/24 X |
| 3,528,424 | 9/1970 | Ayres | 606/19 |
| 3,618,611 | 11/1971 | Urban | 606/170 |
| 3,906,955 | 9/1975 | Roberts | 604/21 X |
| 3,974,833 | 8/1976 | Durden, III | 606/49 X |
| 4,132,227 | 1/1979 | Ibe | 128/4 |
| 4,146,019 | 3/1979 | Bass | 128/6 |
| 4,203,444 | 5/1980 | Bonnell | 606/170 X |
| 4,550,716 | 11/1985 | Kinoshita | 128/6 |
| 4,562,838 | 1/1966 | Walker | 604/22 X |
| 4,587,957 | 5/1986 | Noguchi et al. | |
| 4,598,710 | 7/1986 | Kleinberg et al. | 606/170 |
| 4,601,284 | 7/1986 | Arakawa et al. | 128/6 |
| 4,607,621 | 8/1986 | Wheeler | 128/6 |
| 4,625,713 | 12/1986 | Hiraoka | 128/4 |
| 4,681,561 | 7/1987 | Hood et al. | 604/22 |
| 4,713,051 | 12/1987 | Steppe et al. | 604/30 X |
| 4,719,914 | 1/1988 | Johnson | 606/28 |
| 4,750,902 | 6/1988 | Wunchinich et al. | 604/22 |
| 4,756,309 | 7/1988 | Sachse et al. | 128/6 X |
| 4,844,062 | 7/1989 | Wells | 128/6 X |
| 4,865,018 | 9/1989 | Kanno et al. | 128/6 |

Primary Examiner—William H. Grieb

[57] ABSTRACT

An endoscopic resecting apparatus views and resects a target tissue. The endoscopic resecting apparatus includes a sleeve, a compartmentalized tube, a visualizing device, an illuminating device, a first resecting mechanism, an irrigating apparatus, an aspirating apparatus, a gas insufflation apparatus, and an apparatus to instill a drug. The compartmentalized tube is disposed in the sleeve and has a first compartment of a first set of dimensions and a second compartment of a second set of dimensions larger than the first set of dimensions. A portion of the visualizing device is disposed in the first compartment so that it directly views the target tissue. A portion of the resecting mechanism is disposed in the second compartment so that it resects the target tissue. A portion of the irrigating apparatus is disposed in the first compartment. A portion of the aspirating apparatus is disposed in the second compartment so that it removes the resected target tissue. A portion of the gas insufflation apparatus and the apparatus to instill a drug are disposed in the sleeve. A transducer within the sleeve controls function of the gas insufflation apparatus. The drug instillation apparatus works in conjunction with the gas insufflation apparatus. The visualizing device, illuminating device, first resecting mechanism, irrigating apparatus, and aspirating apparatus are all contained within the same structure in order to function in an integrated and coordinated manner.

15 Claims, 5 Drawing Sheets

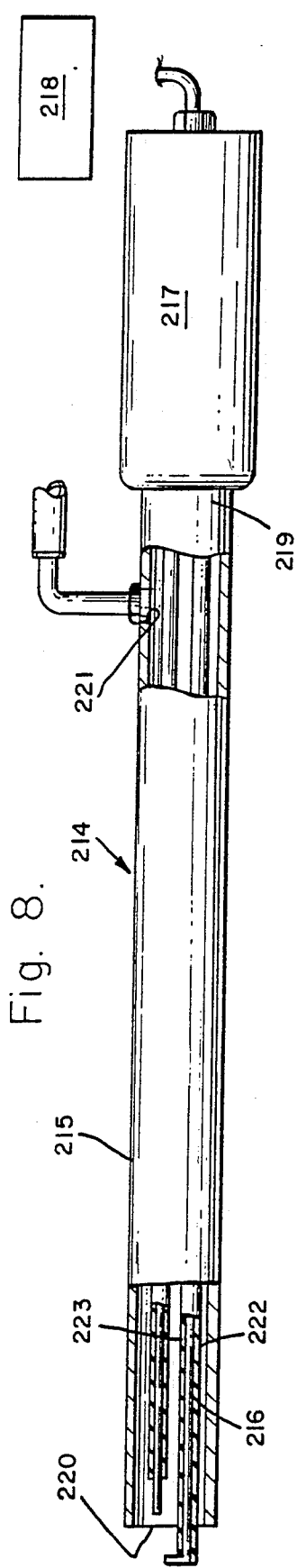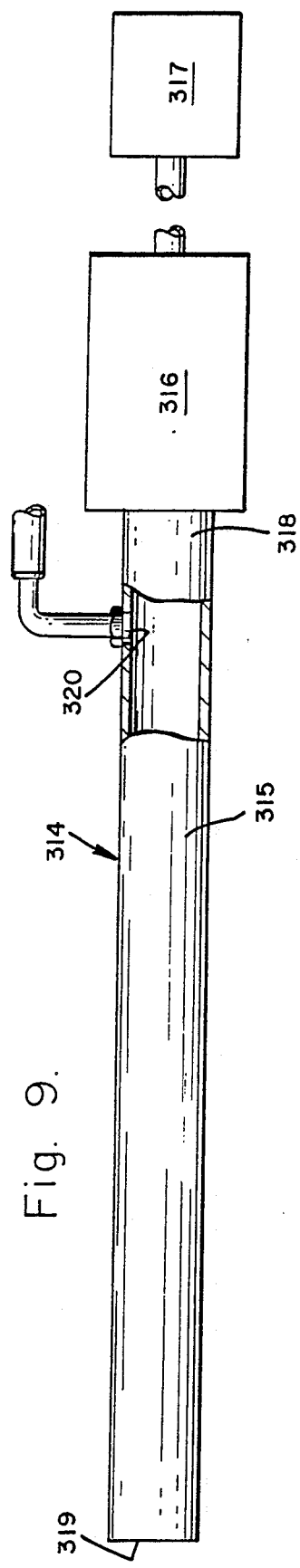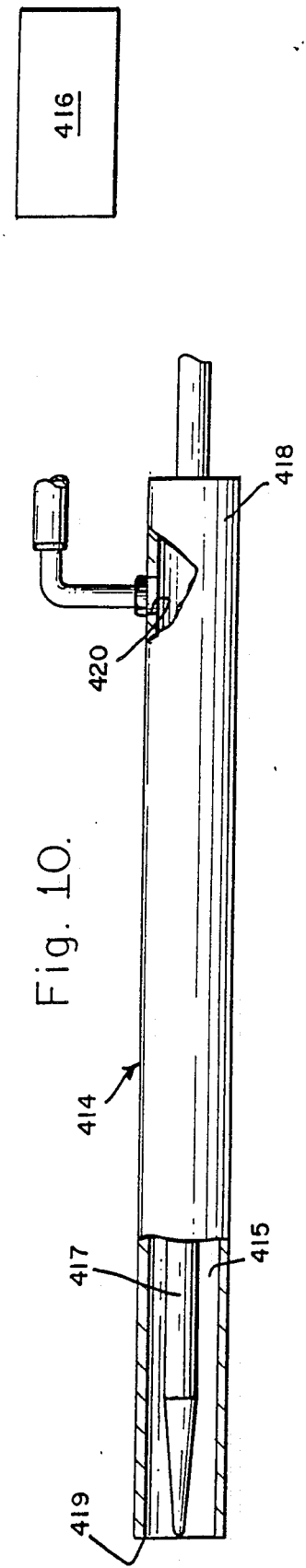

ENDOSCOPIC ABDOMINAL, UROLOGICAL, AND GYNECOLOGICAL TISSUE REMOVING DEVICE

The application is a continuation-in-part of an application, filed Jul. 27, 1989 under Ser. No. 387,577, now abandoned.

BACKGROUND OF THE INVENTION

1. Field of the Invention

This invention relates to an endoscopic resecting system which removes tissue from the abdomen during a general, urological, or gynecological surgical procedure and from the uterus during a hysteroscopic surgical procedure and more particularly to an endoscopic resecting system for permitting visualization into the abdominal cavity or the uterus during tissue resection thereof.

2. Description of the Prior Art

Normal method for surgical removal of pathological tissue from the abdominal cavity is to make a large skin incision over the site within the abdominal cavity where the pathological tissue is located, and dissect into the body through connective tissue, muscle, or other tissues and structures to access the immediate area of the pathology. Then the pathological tissue is actually resected, perhaps including some surrounding healthy tissue, to assure that the entire area of pathology is removed. Finally, connective tissue, muscle, etc. previously dissected through is repaired, sutured together, and the original skin incision is closed. Or a laparoscopic procedure is used in which a medical telescope is inserted into the abdominal cavity along with resecting tools to perform the actual tissue resection.

The laparoscopic technique for removal of pathological substances has significant drawbacks.

Although the laparoscopic device can remove tissue from the abdominal cavity, function of the actual tissue resecting products are inefficient in that either not all of the abnormal tissue is effectively removed, or time to perform the removal is extensive as the hand operated instruments excise only a small volume of tissue each time they bite off a piece of the tissue, and must be constantly removed from the body to clean resected tissue from jaw of the instrument so that it can continue to excise pieces of the pathological material. In addition, larger resecting instruments, although more efficient, are potentially more dangerous in that they can inadvertently also remove normal anatomical structures such as bowel. Also, if any bleeding occurs during resection with hand tools, the procedure must be stopped to control the bleeding, which adds to overall time of surgery.

With most surgical operations of this type, trauma for the patient in the form of post-operative pain and inability to have a normal lifestyle, is caused more by the tissue resection through skin, connective tissue, muscle, etc. to access the pathology than the actual removal of the pathology. In addition, direct medical cost for the post-operative hospital stay, a major component of overall health care cost, is caused more by time to recover from the surgical wounds to access the pathology than from the actual removal of the diseased tissue. Similarly, economic cost of workman's compensation, if a work related injury is involved, for time off from work during recovery to normal, is directly related to the massiveness of the surgical, dissecting wounds. Economic opportunity cost of time off from work, unemployment, or underemployment during recovery from major, open surgery is directly related to extent of the surgical dissection to access pathology, and is significant.

For laparoscopic procedures, general anesthesia is currently used. Some patients complain more about the affects of the anesthesia than the pain associated with removing the pathological tissue.

Prior are for performing certain general, urological, or gynecological surgical procedures within the abdomen are various surgical instruments whose function require that the abdominal cavity be completely exposed by opening it via an incision that extends from just below the diaphragm to the lower abdomen.

Prior art are various surgical devices which have been used, mainly to remove pathological tissue from within body cavities such as the gastrointestinal system, urinary system, orthopaedic joints, etc. These are either single products, or a series of loosely related devices which are used during the operation but which are not coordinated to produce an optimal effect. These devices include medical optical telescopes to view within the body when used in conjunction with light carriers such as a fiber optic bundle, energy form generators and energy form transporters which use electrical, mechanical, laser, etc. energy to cut, burn, or evaporate pathological tissue, suction devices which aspirate the cut pathological tissue from the body, and tubes used to transport these devices into the body cavity.

Additional related prior art is fiber optic light illuminators that are used for medical, endoscopic surgical procedures. Many of these light sources do not provide the light intensity to properly illuminate the abdominal cavity and produce clear images with the medical video camera system that is used in conjunction with the endoscopes.

Additional related prior art is a peristaltic pump used to instill fluid, usually normal saline, into a body cavity to expand its volume, and provide a clear liquid medium to view the body cavity using a generic type of endoscope. This instilled fluid may be removed from the body cavity either through the endoscope or through a separate outflow conduit, usually by applying active suction to the conduit and conecting PVC tubing, the suction being generated by some aspirating external pump. Precise control of rate of inflow is not achieved with prior art instilling pumps, and coordination of volume of inflow to volume of aspiration, through electronic controls is not characteristic of these forms of prior art.

Related prior art is an RF energy electrode introduced separately into the abdominal cavity to control bleeding.

Related prior art are gas insufflators used to expand the abdomen. Although pressure and flow rate from the insufflators can be set and controlled by these machines, measurement of pressure is at the machine, through tubing, and is not measured directly within the abdominal cavity. In addition, no means is provided to instill a treatment drug in the gas which is insufflated, with prior art devices.

Related prior art are machines which function independently including light source illuminators, gas insufflators, and peristaltic pumps, used for surgical procedures other than indicated in this patent application.

Therefore, these devices do not work as efficiently together, extend operating time which increases cost of medical care. Energy form generators and transporters being separate machines, their total cost is greater and they require more effort by personnel to set up and maintain, which also increases cost of medical care.

U.S. Pat. No. 4,132,227, entitled Urological Endoscope Particularly Resectoscope, issued to Wolfgang Ibe on Jan. 2, 1979, teaches a hollow cylinder sheath, a viewing device, an illuminating device, a resecting device and an outflow tube. The hollow cylinder sheath has a proximal end and a distal end. The viewing device is an endoscopic arrangement of optical elements. The illuminating device is a cooperating arrangement of fiber optics which is optically coupled to a light source. The viewing device and the illuminating device are located in the sheath extending from the distal end back to the proximal end. The outflow tube is slidable onto the sheath to surround the sheath and form together with the sheath an intermediate return-flow space between the outer wall of the sheath and the inner wall of the outflow tube, with the outflow tube when in position slid over the sheath tightly surrounding the distal end portion of the sheath. The resecting device is an electrode loop which is electrically coupled to an electromagnetic energy source. Clear rinsing water is introduced into the proximal end of the sheath. Turbid water is removed from the proximal end of the intermediate space. The outflow tube is provided with apertures at the distal end thereof for the flow of clear rinsing water out of the distal end of the sheath and around the end of the endoscope and then through the apertures into the intermediate space. U.S. Pat. No. 4,607,621, entitled Endoscopic Apparatus, issued to Robert C. Wheeler on Aug. 26, 1986, teaches an insertion tube, an electrosurgical generator and an electrode loop which is electrically coupled to the electrosurgical generator.

U.S. Pat. No. 4,713,051, entitled Cassete For Surgical Irrigation And Aspiration And Sterile Package Therefor, issued to Steppe et. al. on Dec. 15, 1987, teaches a cartridge within which is placed an irrigating and irrigating control means, an aspirating and an aspirating control means, and a vacuum and vacuum control means.

U.S. Pat. No. 4,756,309, entitled Endoscope for Removal of Tissue, issued to Hans-Ernst Sachse on Jul. 12, 1988, teaches an endoscope which resects tissue inside body cavities and which includes a hollow outer tube, a rotating shaft and a flushing duct. The shaft carries a grinding or milling head which allows precise removal of scar tissue or other fairly firm tissue under endoscopic control without leaving irregular or thermally damaged wound sites. The endoscope also includes a tube for a lens system and cold light guide and an eyepiece.

U.S. Pat. No. 4,844,062, entitled Rotating Fiberoptic Laser Catheter Assembly with Eccentric Lumen, issued to Lisa D. Wells on Jul. 4, 1989, teaches a catheter assembly which includes a catheter and an optical fiber. The catheter defines a first eccentric lumen which encompasses the center of the catheter and a second lumen. The optical fiber runs through the first eccentric lumen and has a distal end which is eccentric to and encompasses the center of the catheter. U.S. Pat. No. 4,865,018, entitled Control Apparatus for Endoscopes, issued to Masahide Kanno, Katasuyaki Saito and Akihiko Miyazaki on Sept. 12, 1989, teaches a control apparatus which controls a plurality of functions of an endoscope. U.S. Pat. No. 4,550,716, entitled Liquid Supplying Device for Endoscope, issued to Kunio Kinoshita on Nov. 5, 1985, teaches a liquid supplying device which includes a housing with a connecting portion to which a connector of an endoscope is connected. The liquid supplying device also includes a lamp, an air pump, and a liquid supply tank.

U.S. Pat. No. 4,146,019, entitled Multichannel Endoscope, issued to Michael Bass on Mar. 27, 1979 teaches a flexible endoscope with a suction tube that protrudes from the distal end, a laser channel, a fluid delivery channel, and a channel which could accomodate a medical tool. U.S. Pat. No. 4,625,713, issued to Yasunori Hiraoka on Dec. 2, 1986 teaches a device with a trough for collecting and removing debris created when using a resectoscope, including an electode used in conjunction with the trough for coagulating blood. Holes in the trough accomodate an irrigating fluid. The device uses mechanical energy, a slide mechanism to actually remove the debris.

U.S. Pat. No. 3,618,611, entitled Vacuum Rotary Dissector, issued to Julius C. Urban on Nov. 9, 1971, teaches a vacuum rotary dissector which includes a support, an outer tubular member, an inner tubular member and a motor. The outer tubular member extends from the support and has a closed generally hemispherical distal end and a first laterally directed opening adjacent to its distal end extending axially along the outer tubular member and partially along the closed generally hemispherical distal end. The inner tubular member is rotatably mounted in the outer tubular member and has a complementary generally hemisperical distal end frictionally bearing on an inner complementary surface of the closed generally hemispherical distal end of the outer tubular member. The inner tubular member has a second laterally directed opening coextensive with the first laterally directed opening defining generally axially extending cutting edges coincident with the inner surface of the outer tubular member. The motor continuously rotates the inner tubular member relatively to the support and the outer tubular member.

U.S. Pat. No. 4,598,710, entitled Surgical Instrument and Method of Making Same, issued to Larry K. Kleinberg and Donald S. Evans on Jul. 8, 1986, teaches an arthroscopy shaver which includes a pair of co-axially assembled tubes. The tubes have their distal walls in bearing relationship and with registrable openings extending through such distal and annular walls correspondingly joined to their respective distal walls. U.S. Pat. No. 4,203,444, entitled Surgical Instrument Suitable for Closed Surgery Such as of the Knee, issued to Leonard J. Bonnell, Edward H. McHugh, Douglas D. Sjostrom and Lanny L. Johnson on May 20, 1980, also teaches an arthroscopy shaver.

SUMMARY OF THE INVENTION

In view of the foregoing factors and conditions which are characteristic of the prior art it is the primary object of the present invention to provide an endoscopic resecting system which resects pathological material from the abdominal cavity or from near the abdominal cavity while permitting visualization during resection thereof, during a general, urological, or gynecological surgical procedure.

It is another object of the present invention to provide an endoscopic removing system which supports a tissue material removing component in conjunction with an endoscope allowing the tissue material removing component to function properly and protecting the optical component of the endoscope from damage.

It is still another object of the present invention to provide an endoscopic resecting system which instills a transport fluid into or near the abdominal cavity to remove debris away from the end of the endoscope thereby maintaining clear visualization, and transport debris which is created by the tissue resection to the outside of the body.

It is yet another object of the present invention to provide an endoscopic resecting system which is more efficient, more cost effective, easily operated energy source to create and/or deliver into or near the abdominal cavity the proper form of energy for use in performing tissue resection and control of bleeding caused by the tissue resection, thereby reducing operating time while still being able to remove the pathological tissue.

It is yet still another object of the present invention to provide a very high intensity light source as component of the system, which generates appropriate forms and quantity of light sufficient to properly illuminate and/or differentiate structures within or near the abdominal cavity for observation, when a video camera is used in conjunction with the endoscope.

It is still yet another object of the present invention to provide a means for controlled inflow of fluid into and aspiration of fluid from or near the abdominal cavity to maintain clear viewing during the surgical procedure and efficient transport of debris which is created during the resection of the pathological tissue.

It is another object of the present invention to provide a gas inflow system to expand the abdominal cavity which automatically instills a drug along with the gas consisting of a gas insufflator, device to inject the drug along with the gas, connecting tubing, and a transducer located within a conduit placed into the abdominal cavity, to distend the abdominal cavity, and accurately maintain pressure by measuring it within the abdominal cavity.

It is still another object of the present invention to provide a combination of endoscope and video camera in one integral device to view within the abdominal cavity.

It is still a further object of the present invention to provide an interrelated and coordinated system of energy sources within the same physical chasis including light source, energy source to resect the pathological tissue, energy source to inflow and control aspiration of a transporting medium, and gas insufflation with potential for drug instillation, with the chasis modularized for efficient service.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 8 is a longitudinal view in cross-section of second resecting mechanism of a second endoscopic resecting system which includes a console and an endoscopic viewing and resecting apparatus and which has been made in accordance with the principles of the second embodiment of the present invention.

FIG. 9 is a longitudinal view of a third resecting mechanism of a third endoscopic resecting system which includes a console and an endoscopic viewing and resecting apparatus and which has been made in accordance with the principles of the third embodiment of the present invention.

FIG. 10 is a longitudinal view of a fourth resecting mechanism of a fourth endoscopic resecting system which includes a console and an endoscopic viewing and resecting apparatus and which has been made in accordance with the principles of the fourth embodiment of the present invention.

DESCRIPTION OF THE PREFERRED EMBODIMENT

Figure 1:
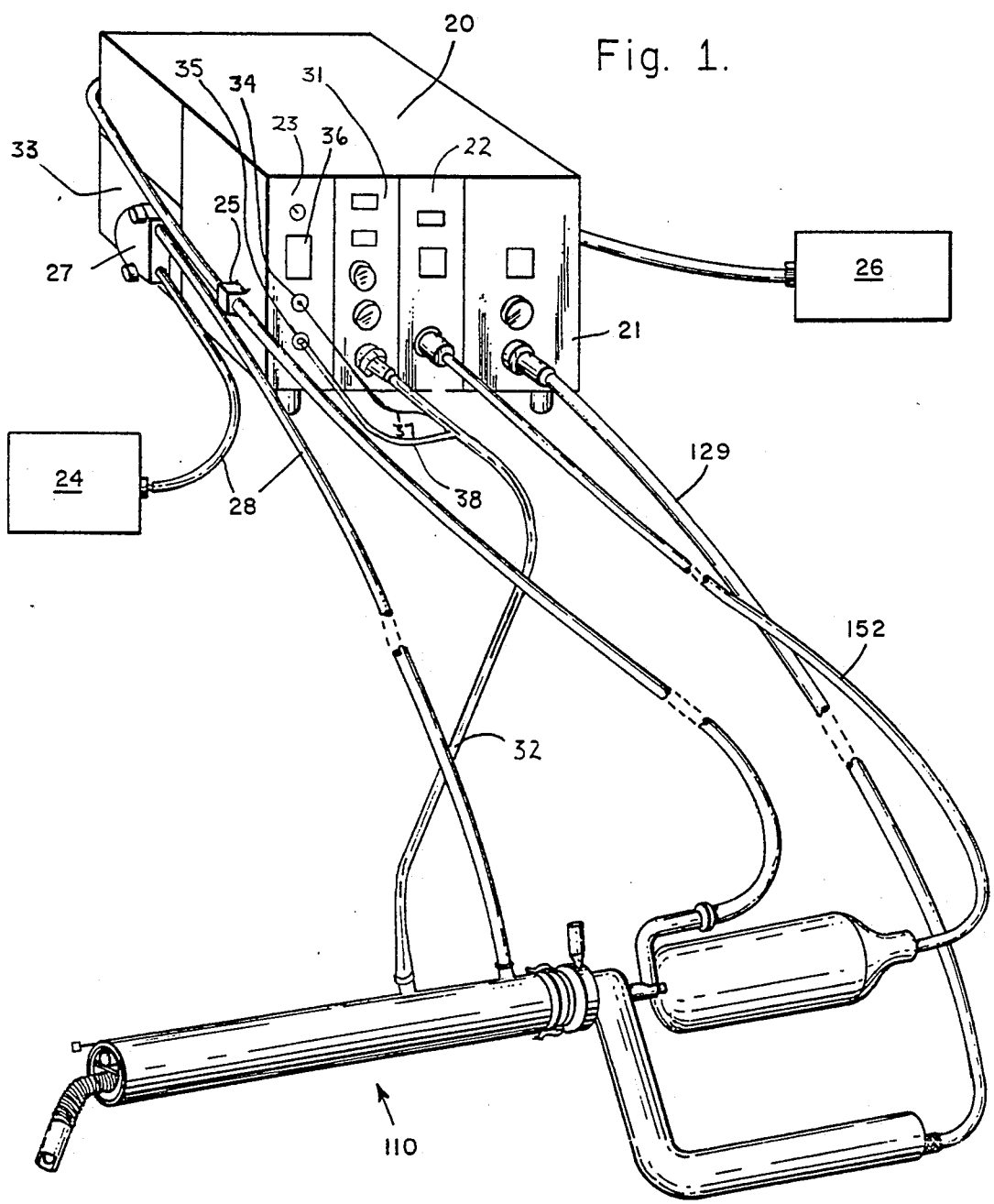
FIG. 1 is a perspective drawing of a first endoscopic resecting system which includes a console and a first endoscopic viewing and resecting apparatus and which has been made in accordance with the principles of the first embodiment of the present invention.

In order to best understand the present invention it is necessary to refer to the following description of its preferred embodiment in conjunction with the accompanying drawing. Referring to FIG. 1 an endoscopic resecting system 10 includes a console 20 and an endoscopic viewing and resecting apparatus 110 for viewing and resecting a target tissue from the area within or near the abdominal cavity or from within the uterus. The console 20 includes at least six separate modules which are a light source module 21, a motor module 22, a drug instillation control module 23, a transport medium peristaltic pump module 33, and a gas insufflator controls module 31. An alternative embodiment includes a video image signal processing module. On the front side of the light source module 21 are its operating controls which include an on/off toggle power switch, a light source intensity digital read-out, an intensity adjusting rheostat, and a fiber optic cable connection. On the front side of the motor module 22 are its operating controls which include an on/off toggle power switch, a motor speed adjustment, and a motor handpiece connection. The electronic components of the motor module 22 include a connection to a 110 volt external power supply, an on/off toggle power switch, a printed circuit board, a transformer, a heat sink, a speed adjusting control and motor handpiece connection. The console 20, which is electrically coupled to a 110 volt external power supply, also includes an on/off toggle power switch, a power supply, a lamp, a lamp cooling fan, a digital read-out of intensity, and a protecting glass and a light intensity measuring device. The non-electronic components of the console 20 also include support brackets for the power supply, the rheostat used to adjust light intensity, the aperture plate, the light attenuator, the fiber optic cable holder and the lourves near the lamp and in line with air flow from the fan.

Still referring to FIG. 1 on the front side of the drug instillation controls module 23 are the transducer wire connection to the module 34, instilled drug reservoir 36, drug instilling rate adjusting rheostat, and drug instillation line connection to the module 35. The drug instillation line connection 35 is mechanically and fluidly coupled to the drug instillation line 38. The drug instillation line 38 is further fluidly and mechanically connected to the gas insufflation line 32. The transducer wire connection to the module 34 is mechanically and electronically coupled to the transducer wire 37. The transducer wire 37 is further mechanically and electronically coupled to the to the gas insufflation line 32. On the side of the drug instillation controls module 23 is a suction tube occluding device 25 which regulates suction pressure from a suctioning apparatus 26. The tube occluding device 25 is adjusted to regulate the outflow of the saline and the resected tissue from the surgical site. The drug instillation controls module 23 includes a connection to a 110 volt external power supply, an on/off toggle power switch, an inflow rate digital read-out, an inflow rate adjusting rheostat, a printed circuit board for the pump and controls, a printed circuit board for the suction controls, and a suction pressure adjusting rheostat. On the side of the peristaltic pump module 33 is a pump tubing holder 27 which is mechanically coupled to inflow tubing 28. A saline source 24 is fluidly coupled to the inflow tubing 28. The electronic components of the peristaltic pump module 33 include a connection to pump controls module, a transformer and a motor. The non-electronic components of the peristaltic pump module 33 include a system of torque dampeners, a pump driver, the peristaltic action producing wheel and a mechanical connector from motor shaft to peristaltic action producing wheel. Electronic components of the gas insufflator module 31 include on/off power toggle switch, flow rate adjusting rheostat, pressure adjusting rheostat, digital read-out of the flow rate and digital read-out of pressure. Externally placed electronic components of the alternative embodiment video image signal processing module include on/off power toggle switch and connection of the signal carrying cord to the front of the module.

Figure 2:
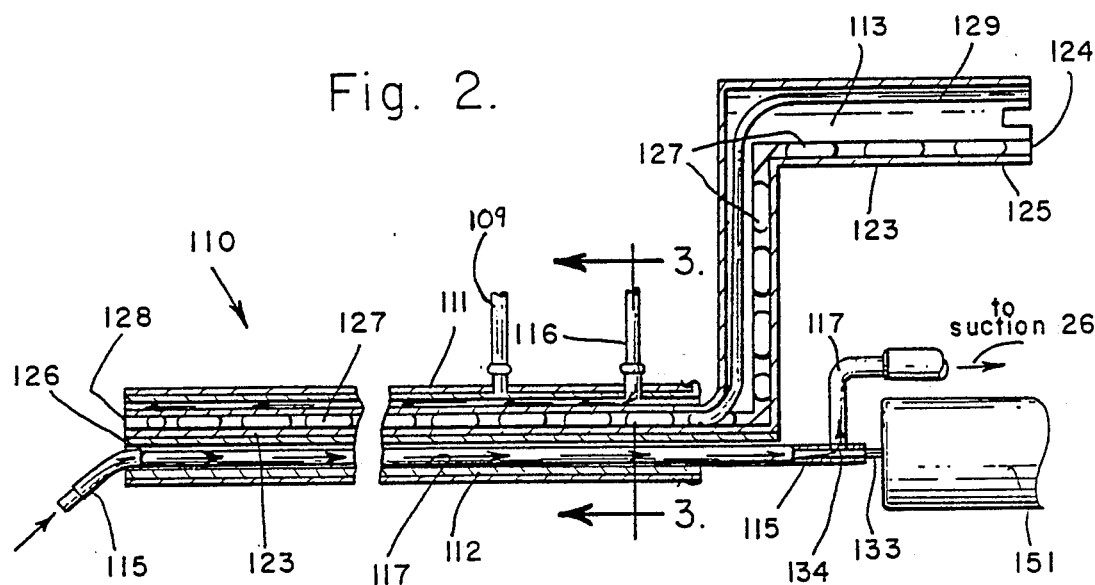
FIG. 2 is a partial longitudinal cross-sectional view of the first endoscopic viewing and resecting apparatus of FIG. 1 which includes a compartmentalized tube, a barrier between the compartments of the tube, a visualizing device, an illuminating device and a first resecting mechanism.
Figure 3:
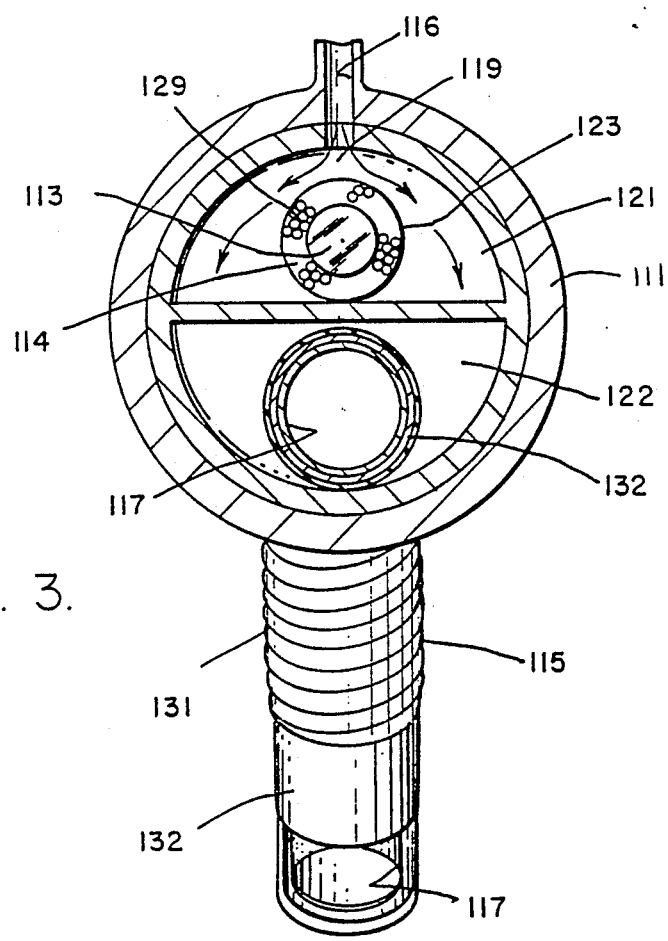
FIG. 3 is a transverse cross-sectional view of the first endoscopic viewing and resecting apparatus of FIG. 1 taken along the line 3—3 of FIG. 2 which also includes a compartmentalized tube, a barrier between the compartments of the tube, an irrigating apparatus and an aspirating outflow apparatus.

Referring to FIG. 2 in conjunction with FIG. 1 and 3 the endoscopic viewing and resecting apparatus 110 includes a sleeve 111, a compartmentalized tube 112, a gas inflow apparatus 109, a visualizing device 113, an illuminating device 114, a first resecting mechanism 115, an irrigating apparatus 116, and an aspirating apparatus 117. The suctioning apparatus 26, which is provided in the operating room, is fluidly coupled to the aspirating apparatus 117. The irrigating apparatus 116 has an inflow connector 118 which is mechanically coupled to the compartmentalized tube near its proximal end and which is fluidly and mechanically coupled to the saline source 24 by the inflow tubing 28. The gas inflow apparatus is mechanically and pneumatically coupled to the gas insufflator controls module 31 by gas tubing 32.

Figure 4:
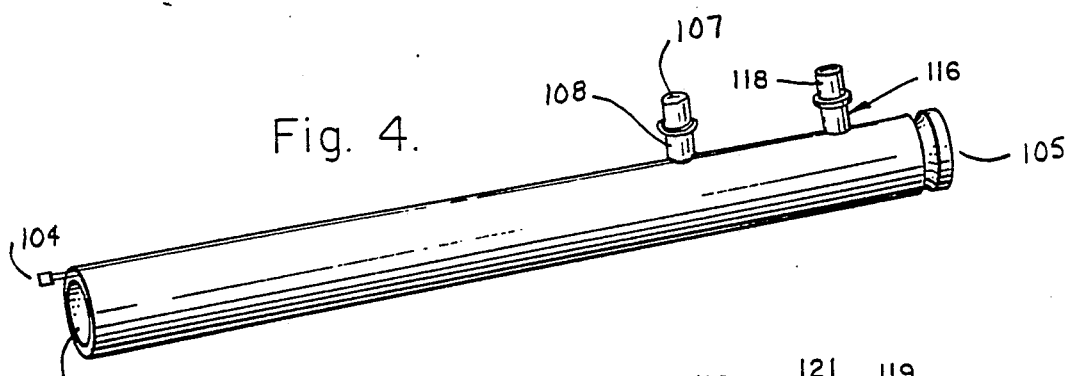
FIG. 4 is a perspective drawing of the sleeve of the first endoscopic viewing and resecting apparatus of FIG. 1 into which the compartmentalized tube is inserted.

Referring to FIG. 4 in conjunction with FIG. 1 the sleeve has a proximal end 105 and a distal end 106. The compartmentalized tube 122 is introduced into the abdominal cavity through the sleeve. The sleeve has a gas inlet 107 near the proximal end 105. The gas inlet 107 inlets gas from the gas insufflator module 31 through the gas tubing 32. The gas inlet 107 is mechanically and pneumatically coupled to the gas insufflator module 31 through the gas tubing 32. The sleeve has a transducer 104 at the distal end 106. The transducer 104 measures intra-abdominal pressure during the operation.

Figure 5:
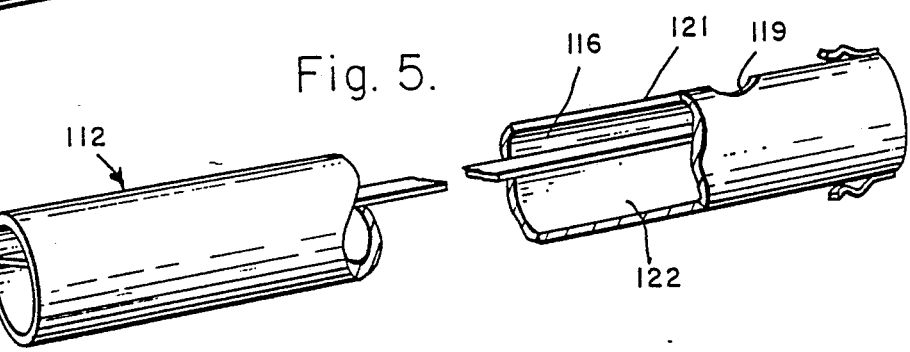
FIG. 5 is a partial perspective drawing of the compartmentalized tube and barrier of the first endoscopic viewing and resecting apparatus of FIG. 1.

Referring to FIG. 5 in conjunction with FIG. 2 and FIG. 3 the compartmentalized tube 112 has a first compartment 121 of a first set of dimensions, a second compartment 122 of a second set of dimensions larger than the first set of dimensions, and a barrier 125 between the first and second compartments. The visualizing device 113 directly views the target tissue. A portion of the visualizing device 113 is disposed in the first compartment 121. The illuminating device 114 provides illumination of the target tissue. A portion of the illuminating device 114 is disposed in the first compartment 121. The first resecting mechanism 115 resects the target tissue. A portion of the first resecting mechanism 115 is disposed in the second compartment 122. The inlet 116 inlets a transport fluid to the resected target tissue. The outlet 117 outlets the transport fluid to a suctioning device 26. A portion of the outlet 117 is disposed in the second compartment 122. The visualizing device 113, the illuminating device 114, the first resecting mechanism 115, the inlet 116, and the outlet 117, all function is an integrated and coordinated manner. The visualizing device 113 includes a hollow metal sheath 123 and an eyepiece 124. A portion of the hollow metal sheath 123 is disposed in the first compartment 121. The eyepiece 124 is mechanically and optically coupled to the hollow metal sheath 123 at its proximal end 125. The eyepiece 124 is disposed at an angle and adjacent to the resecting mechanism 115. The visualizing device 113 includes a lens train 127 and a focusing lens 128. The lens train 127 has a plurality of lenses and is mechanically and optically coupled to the eyepiece 124 and disposed in the hollow metal sheath 123. The focusing lens 128 is mechanically and optically coupled to the lens train 127 and disposed in the hollow metal sheath 123 at its distal end 126. In an alternative embodiment the visualizing device 113 may include a coherent optical fiber and a focusing lens. The coherent optical fiber is mechanically and optically coupled to the eyepiece 124 and disposed in the metal sheath 123. The focusing lens 128 is mechanically and optically coupled to the coherent optical fiber and disposed in the metal sheath 123 at its distal end 126. A small video camera may be attached to the eyepiece 124. In another alternative embodiment the visualizing device may include a video chip, preamplifier, and other electronics in the metal sheath 123 at its distal end 126. The electronics at the distal end 126 are mechanically and electronically coupled to the alternative embodiment video imaging processor module. The illuminating mechanism 114 includes an optical fiber 129 and a light generator 21. A portion of the optical fiber 129 is disposed within the metal sheath 123 parallel to the lens train and is optically aligned with the lens train 127. U.S. Pat. No. 4,601,284, entitled Endoscope Connecting System, issued to Satoshi Arakawa and David H. Cooper on Jul. 22, 1986, teaches a video camera which is optically coupled to an eyepiece, an optical-fiber connector which is disposed orthogonally to the eyepiece and a optical fiber. This is the standard arrangement of the prior art because the optical fiber needed to be out of the way of the surgeon's eye during endoscopy. Most endoscopy is now performed with a video monitor. In the present invention the eyepiece 124 and optical fiber 129 are disposed contiguously and parallel to one another so that a single cable bundle to the console 20 may be used. The light generator 21 generates light and is mechanically and optically coupled to the optical fiber 129. The illuminating device 114 provides illumination of the target tissue. A portion of the illuminating device 114 is disposed in the first compartment 121. The visualizing device 113, the illuminating device 114, the first resecting mechanism 115, the irrigating apparatus 116 and the aspirating apparatus 117 all function in an integrated and coordinated manner.

Figure 6:
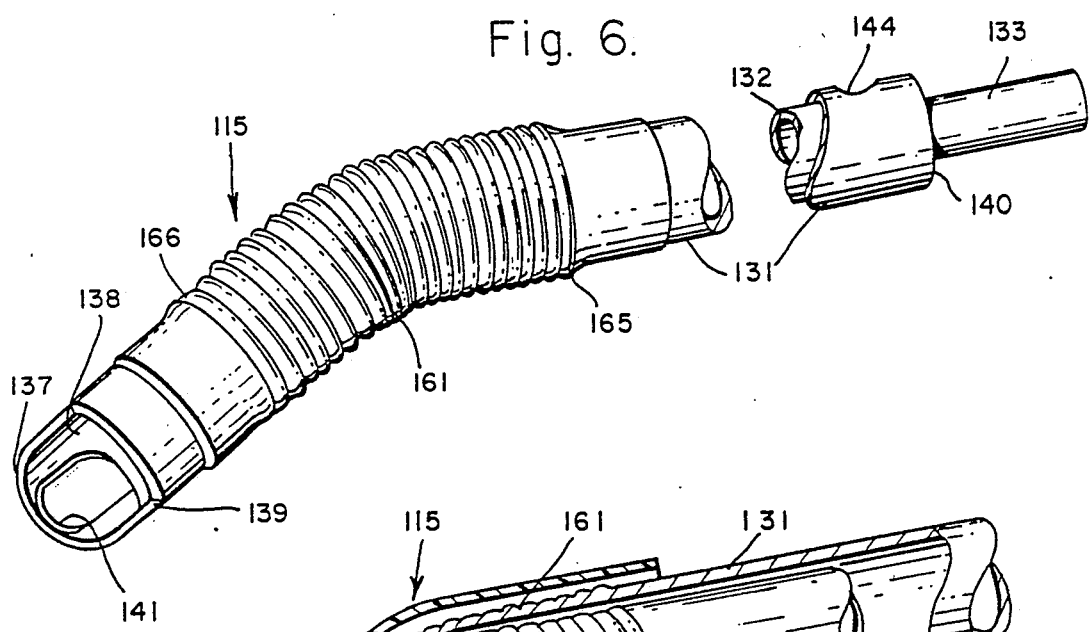
FIG. 6 is a partial perspective drawing of the first resecting mechanism of the first endoscopic viewing and resecting apparatus of FIG. 1.
Figure 7:
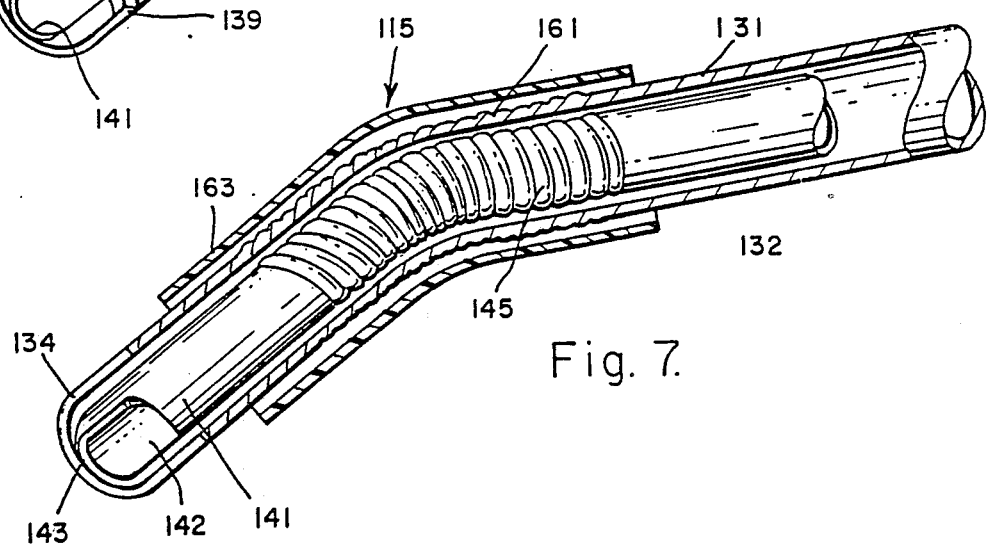
FIG. 7 is a partial longitudinal view in cross-section of the first resecting mechanism of the first endoscopic viewing and resecting apparatus of FIG. 1.

Referring to FIG. 2 in conjunction with FIG. 3, FIG. 6, and FIG. 7 the first resecting mechanism 115 may include a hollow tube 166 and a driving mechanism 165, or an outer tube 131, an inner tube 132, and driving mechanism 133. The hollow tube 166 has a proximal end 161 and a distal end 162 and is disposed in the second compartment 122. The hollow tube 166 has an open distal end 163 and a cutting blade 164 just proximal to the open distal end 163. The hollow tube 166 has a window 167 near its proximal end. The driving mechanism 165 rotatively drives the hollow tube 166 so that the cutting blade 164 resects the target tissue. The resected target tissue and the transport medium are then aspirated into the hollow tube 166 at the open distal end 163 of the hollow tube 166 and then move through the lumen 168 of the hollow tube 166 to the window 167 near the proximal end 161 of the hollow tube 166. The outer tube 131 has a proximal end 136 and a distal end 137 and is disposed in the second compartment 122. The outer tube 131 has a first slot 138 with a first peripheral edge 139 at its distal end 137. The inner tube 132 has a proximal end 140 and a distal end 141 and is disposed coaxially with and rotatively coupled to the outer tube 131. The inner tube 132 has a second slot 142 with a second peripheral edge 143 at its distal end 141 and a window 144 at its proximal end 140. The driving mechanism 133 rotatively drives the inner tube 132 so that the first 139 and second 143 peripheral edges articulate thereby resecting the target tissue. The resected target tissue and transport medium are then aspirated into the lumen 146 of the inner tube 132 at the second slot 142 near the distal end 141 of the inner tube 132. The target tissue moves through the lumen 146 of the inner tube 132 to the window 144 near the proximal end 140 of the inner tube 132. The driving mechanism 133 includes an electric motor 151 and a power cord 152 the distal end of which is connected to the motor module 22. The window 144 is disposed adjacent to the outlet connector 134.

Referring to FIG. 8 a second resecting mechanism 214 includes a tube 215, an active electrode 216, a handpiece 217 and a generator 218. The tube 215 has a proximal end 219 and a distal end 220. A portion of the tube 215 is disposed in the second compartment 122 and has a window 221 at its proximal end 219. The outer surface 222 of the active electrode 216 is coated with a layer 223 of insulating material. A portion of the active electrode 216 is disposed within the tube 215. The active electrode 216 may be either monopolar or bipolar. The generator 218 generates electromagnetic energy in the radio frequency spectrum and is electrically coupled to the active electrode 216 so that the active electrode 216 is heated in order to resect the target tissue. U.S. Pat. No. 4,719,914, entitled Electrosurgical Instrument, issued to Gerald W. Johnson on Jan. 19, 1988, teaches an electrosurgical instrument. Each of U.S. Pat. Nos. 4,562,838, 3,974,833, 3,906,955, 3,828,928 teaches an electrosurgical instrument which has a tube and an electrode for use in high frequency electrocoagulation. The tube either supplies a liquid to the surgical site or aspirates blood and fluid, liquid and/or smoke from the surgical site.

Referring to FIG. 9 a third resecting mechanism 314 includes a tube 315, a transducer 316 and a generator 317. The tube 315 has a proximal end 318 and a distal end 319 and which is disposed in the second compartment 122. The tube 315 has a window 320 at its proximal end 318. The transducer 316 is mechanically coupled to the tube 314 and disposed at its proximal end 318. The generator 317 generates ultrasonic energy and is electrically coupled to the transducer 316 so that the transducer 316 causes the tube 315 to resonate in order to resect the target tissue. U.S. Pat. No. 4,750,902, entitled Endoscopic Ultrasonic Aspirators, issued to David G. Wuchinich, Robert Brendolan, Louis Katz, Donald R. Krawitt on Jun. 14, 1988, teaches an endoscopic ultrasonic aspirator for removal of compliant biological tissues which includes irrigation and aspiration apparatus, a tube and a piezoelectric ultrasonic transducer. U.S. Pat. No. 4,681,561, entitled Ultrasonic Decoupling Sleeve, issued to Larry L. Hood and Maurice M. Imonti on Jul. 21, 1987, teaches a decoupling sleeve for inclusion in a fluid conduit of an ultrasonically-operated surgical instrument. U.S. Pat. No. 4,587,957, entitled Ultrasonic Surgical Device, issued to Yasuo Noguchi and Masaru Shibata on May 13, 1986, teaches an ultrasonic surgical device which includes an ultrasonic transducer and a horn through which an irrigation fluid and surgical debris flow from the surgical site.

Referring to FIG. 10 a fourth resecting mechanism 414 includes a tube 415, a laser 416, and a lightguide 417. The tube 415 has a proximal end 418 and a distal end 419 and is disposed in the second compartment 122. The tube 415 has a window 420 at its proximal end 418. The laser 416 generates light energy. The light guide 417 is disposed in the tube 415 and guides the light energy so that the conversion of light energy to heat resects the grouting agent or osseus tissue. U.S. Pat. No. 3,528,424, entitled Laser Surgical Knife Equipment, issued to Waldemar A. Ayres on Sept. 15, 1979, teaches a laser generator and a light guide in conjunction with an articulated arm. Although the laser generator of U.S. Pat. No. 3,528,424, is a carbon dioxide laser, other laser generators including, but not limited to, an excimer laser, a ruby laser, an argon laser, and erbium:YAG laser and a neodymium:YAG laser with an without a contact sapphire tip may be used.

Figure 11:
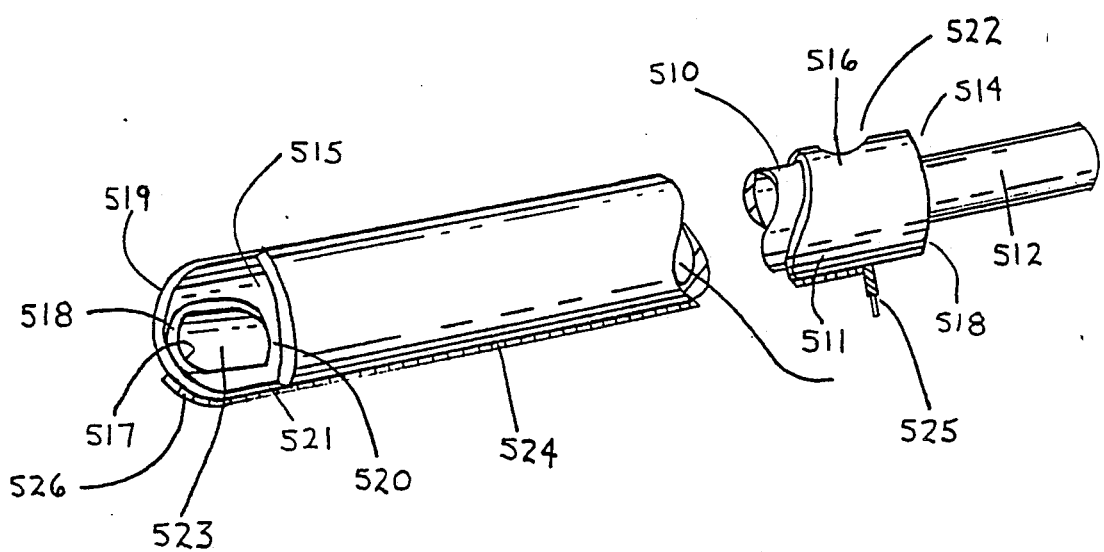
FIG. 11 is a longitudinal view of a fifth resecting mechanism of a fifth endoscopic resecting system which includes a console and an endoscopic viewing and resecting apparatus and which has been made in accordance with the principles of the fifth embodiment of the present invention.

Referring to FIG. 11 in conjunction with FIG. 2 and FIG. 3 the fifth resecting mechanism includes an inner tube 510, an outer tube 511, and a driving mechanism 512 and resects the target tissue. A portion of the fifth resecting mechanism is disposed in the second compartment 122 when the first resecting mechanism is not in place in the second compartment 122. The inner tube 510 has a proximal end 514 and a distal end 515. The inner tube 510 has a window 516 at its proximal end 514 and a first slot 517 with a first peripheral edge 518 at its distal end 515. The outer tube 511 has a proximal end 518 and a distal end 519 and is disposed coaxially with and rotatively coupled to the inner tube 510. The outer tube 511 has a second slot 520 with a second peripheral edge 521 at its distal end 519 and a window 522 at its proximal end 518. The driving mechanism 133 rotatively drives the inner tube 132 so that the first and second peripheral edges 518 and 521 articulate thereby resecting the target tissue. The resected target tissue is aspirated into the lumen 523 of the inner tube 510. The window 522 is disposed adjacent to the outlet connector. The outer tube 511 has an active electrode 524 which is coated with an insulating material. The outer tube 511 has a high frequency cord connector 525 near the proximal end 518 and a portion of uninsulated active electrode 526 at the distal end. The active electrode 524 may be either monopolar or bipolar. The generator 218 generates electromagnetic energy in the radio frequency spectrum and is electrically coupled to the active electrode 524 so that the active electrode 524 is heated in order to coagulate bleeding blood vessels.

Accordingly, the endoscopic resecting system 10 can be used to remove a target tissue from within the abdominal cavity or near the abdominal cavity under direct visual control. All of the energy sources for illumination, target tissue removal, transportation of debris, control of gas insufflation, and control of instillation of a drug treatment are conveniently located in the same modularized console 20 so that these processes of the operation are controlled and coordinated. The components of the endoscopic resecting system 10 placed partially within the body are organized in order to minimize the outer diameter of the compartmentalized tube 24 while still coordinating all of these functions to efficiently and quickly complete the target tissue removal process.

Direct visual control of the target tissue removal process reduces the need to make large incisions into the body which in turn reduces pain, suffering, and surgical morbidity and also reduces the cost of direct medical care and the overall cost while patients recover from an open operation.

The endoscopic resecting system 10 permits the surgeon to directly view within the abdominal cavity or near the abdominal cavity to observe removal of a target tissue in order to assure that it completely removes the target tissue. The endoscopic resecting system 10 also incorporates a mechanism for allowing inflow and aspiration of a transport medium to effectively extract debris created by the target tissue resecting process obviating the need to perform major open surgery which involves extensive hospital stay, extended time to recovery, and much higher cost for medical care.

During the target tissue removing process pressure within the abdominal cavity is directly controlled by placing a pressure sensing transducer within the abdominal cavity. A drug can be administered during the operation directly into the abdominal cavity through the gas insufflation mechanism. Bleeding from blood vessels which occurs during the target tissue removal can be controlled using the resecting mechanism that has an active electrode.

From the foregoing it can be seen that an endosopic resecting system 10 has been described. It should be noted that the sketches are not drawn to scale and that distance of and between the figures are not to be considered significant.

What is claimed is:
1. An endoscopic resecting system for viewing and resecting a target tissue from within or near the abdominal cavity, said endoscopic resecting system comprising:
   a. a sleeve
   b. a compartmentalized hollow tube with a first compartment of a first set of dimensions and a second compartment of a second set of dimensions larger than said first sets of dimensions;
   c. visualizing means for directly viewing the target tissue, a portion of said visualizing means being disposed in said first compartment;
   d. illuminating means for providing illumination of the target tissue, a portion of said illuminating means being disposed in said first compartment;
   e. resecting means for resecting the target tissue, a portion of said resecting means being disposed in said second compartment;
   f. inletting means for inletting a transport fluid to said resected target tissue, a portion of said inletting means being disposed in said first compartment; and
   g. outletting means for outletting said transport fluid to the suction device, a portion of said outletting means being disposed in said second compartment whereby said visualizing means, said illuminating means, said resecting means, said inletting means and said outletting means all function in an integrated and coordinated manner;
   h. gas insufflation means for expanding the abdomen, a portion of said gas insufflation means being disposed within said sleeve.
   i. means to apply a drug treatment, said drug treatment means being disposed within said gas insufflation means;
   j. blood coagulating means, a portion of said coagulating means being mechanically connected to said resecting means.

2. An endoscopic resecting system for viewing and resecting a target tissue according to claim 1 wherein said sleeve comprises:
   a. a tube which has a proximal end and a distal end;
   b. a gas inflowing mechanism which is mechanically coupled to said tube near its said proximal end;
   c. a pressure sensing transducer which is mechanically coupled to said tube at its said distal end.
   d. an electrical connector which is mechanically coupled to said tube near its said proximal end and is electrically coupled to said transducer; and
   e. an electrical wire disposed from said transducer at said distal end to said electrical connection near said proximal end of said tube.

3. An endoscopic resecting system for viewing and resecting a target tissue according to claim 1 wherein said visualizing means comprises;
   a. a hollow metal sheath which has a proximal end and a distal end and a portion of which is disposed in said first compartment;
   b. an eyepiece which is mechanically and optically coupled to said hollow metal sheath at its said proximal end, said eyepiece being disposed at an angle and adjacent to said resecting means;
   c. a lens train which has a plurality of lenses and which is mechanically and optically coupled to said eyepiece and disposed in said hollow metal sheath; and d. a focusing lens which is mechanically and optically coupled to said lens train and disposed in said hollow metal sheath at its said distal end.

4. An endoscopic resecting system for viewing and resecting a target tissue according to claim 1 wherein said visualizing means comprises:

a. a metal sheath which has a proximal end and a distal end and a portion of which is disposed in said first compartment;

b. an eyepiece which is mechanically and optically coupled to said hollow metal sheath at its said proximal end, said eyepiece being disposed at an angle and adjacent to said resecting means;

c. a coherent optical fiber which is mechanically and optically coupled to said eyepiece and disposed in said hollow metal sheath; and d. a focusing lens which is mechanically and optically coupled to said coherent optical fiber and disposed in said hollow metal sheath at its said distal end.

5. An endoscopic resecting system for viewing and resecting a target tissue according to claim 1 wherein said visualizing means comprises:

a. a metal sheath which has a proximal end and a distal end and a portion of which is disposed in said first compartment;

b. a focusing lens which is disposed in said metal sheath at its said distal end;

c. a video imaging chip and image transmitting electronics which are disposed in said metal sheath near its said distal end;

d. electrical wires which are disposed in said metal sheath from near its said distal end to its said proximal end.

6. An endoscopic resecting system for viewing and resecting a target tissue according to claim 1 wherein said resecting means comprises:

a. an outer tube which has a proximal end and a distal end and which is disposed in said second compartment, said outer tube having a first slot with a first peripheral edge at its said distal end, a window near its said proximal end, and a flexible portion near its said distal end;

b. an inner tube which has a proximal end and a distal end and which is disposed coaxially with and rotatively coupled to said outer hollow tube, said inner tube having a second slot with a second peripheral edge at its said distal end, a window at its said proximal end and a flexible portion near its said distal end; and c. driving means for rotatively driving said inner tube so that said first and second peripheral edges articulate thereby resecting the target tissue.

7. An endoscopic resecting system for viewing and resecting a target tissue according to claim 1 wherein said resecting means comprises:

a. an outer tube which has a proximal end and a distal end and which is disposed in said second compartment, said outer tube having a first slot with a first peripheral edge at its said distal end and an active electrode disposed along its length from said distal end to said proximal end;

b. an inner tube which has a proximal end and a distal end and which is disposed coaxially with and rotatively coupled to said outer tube, said inner tube having a second slot with a second peripheral edge at its said distal end and a window at its said proximal end; and c. driving means for rotatively driving said inner tube so that said first and second peripheral edges articulate thereby resecting the target tissue.

8. An endosopic resecting system for viewing and resecting a target tissue according to claim 2 wherein said illuminating means comprises:

a. An optical fiber a portion of which is disposed within said hollow metal sheath and which is optically aligned with said lens train; and b. a light generating means for generating light which is mechanically and optically coupled to said optical fiber.

9. An endoscopic resecting system for viewing and resecting a target tissue according to claim 3 wherein said illumination means comprises:

a. an optical fiber a portion of which is disposed within said hollow metal sheath and which is optically aligned with said coherent optical fiber; and b. a light generating means for generating light which is mechanically and optically coupled to said optical fiber.

10. An endoscopic resecting system for viewing and resecting a target tissue according to claim 1 wherein said resecting means comprises:

a. a tube which has a proximal end and a distal end and the outer surface of which is coated with a layer of insulating material, a portion of said tube being disposed in said second compartment and having a window at its said proximal end;

b. an active electrode which is coated with a layer of insulating material and a portion of which is disposed within said tube; and c. generating means for generating electromagnetic energy in the radio frequency spectrum, said generating means being electrically coupled to said active electrode so that said active electrode is heated in order to resect the target tissue.

11. An endoscopic resecting system for viewing and resecting a target tissue according to claim 1 wherein said resecting means comprises:

a. a tube which has a proximal end and a distal end and which is disposed in said second compartment, said tube having a window at its said proximal end;

b. a transducer which is mechanically coupled to said tube and disposed at its said proximal end; and c. generating means for generating ultrasonic energy in the radio frequency spectrum, said generating means being electrically coupled to said transducer so that said transducer causes said tube to resonate in order to resect the target tissue.

12. An endoscopic resecting system for viewing and resecting a target tissue according to claim 1 wherein said resecting means comprises:

a. a tube which has a proximal end and a distal end and which is disposed in said second compartment, said tube having a window at its said proximal end;

b. a laser which generates light energy;

c. a light guide which is disposed in said tube and is optically coupled to said laser so that conversion of said light energy to heat resects the target tissue.

13. An endoscopic resecting system for viewing, resecting, and removing a target tissue according to claim 1 wherein said removing means comprises:

a. an electronically controlled pump which pumps a transport fluid to a resected target tissue;

b. tubing connecting said pump to an inletting means;

c. inletting means for inletting a transport fluid to said resected target tissue, a portion of said inletting means being disposed in a first compartment;

d. a hollow tube which has a proximal end and a distal end, a slot at its distal end and a window at its proximal end, which outlets the resected target tissue and transport fluid;

e. a mechanism connecting said window to additional tubing;

f. tubing connecting said mechanism to an electronically controlled suction regulating device;

g. an electronicaly controlled suction regulating device which controls suction of said resected target tissue and transport fluid;

h. additional electronic controls coordinating rate of inflow of the transport fluid to rate of suction of the transport fluid.

14. A resecting apparatus comprising:

a. an outer tube which has a proximal end and a distal end and which has a flexible portion near its said distal end, said flexible portion being formed out of spirally shaped coil with said outer tube having a first slot with a first peripheral edge at its said distal end;

b. a plastic covering which covers said flexible portion of said outer tube;

c. an inner tube which has a proximal end and a distal end and which has a flexible portion near its said distal end, said flexible portion being formed out of spirally shaped coil, with said inner tube being disposed coaxially with and rotatively coupled to said outer tube, said inner tube having a second slot with a second peripheral edge at its said distal end and a window at its proximal end; and d. driving means for rotatively driving said inner tube so that said first and second peripheral edges articulate thereby resecting the target tissue.

15. A gas inflow system comprising:

a. a sleeve;

b. gas inflow means mechanically and pneumatically coupled to said sleeve;

c. a pressure sensing transducer pneumatically coupled to said gas inflow means and mechanically coupled to said sleeve at its distal end;

d. an electrical connector which is mechanically coupled to said sleeve near its proximal end and electrically coupled to said transducer;

e. an electrical wire disposed from said transducer at the distal end of said sleeve to said electrical connector at the proximal end of said sleeve;

f. a machine containing pressure controlling means that is electrically connected to said transducer, and containing electronic control devices that adjust pressure based on pressure measured by said transducer; and g. a machine containing gas flow rate controlling means that is electrically connected to said transducer, and containing electronic control devices that adjust flow rate based on pressure measured by said transducer.

* * * * *